(12) United States Patent
Richardson et al.

(10) Patent No.: US 12,709,631 B2
(45) Date of Patent: Aug. 18, 2026

(54) FILTRATION UNIT AND A METHOD FOR BIOMATERIAL PURIFICATION

(71) Applicant: Solventum Intellectual Properties Company, Maplewood, MN (US)

(72) Inventors: Kristopher E. Richardson, Inver Grove Heights, MN (US); Daniel J. O'Neal, St. Paul, MN (US); Jerald K. Rasmussen, Woodville, WI (US); Andrew W. Vail, Bayport, MN (US); Alexei M. Voloshin, Woodbury, MN (US)

(73) Assignee: Life Technologies Corporation, Carlsbad, CA (US)

( * ) Notice: Subject to any disclaimer, the term of this patent is extended or adjusted under 35 U.S.C. 154(b) by 643 days.

(21) Appl. No.: 18/251,412

(22) PCT Filed: Nov. 8, 2021

(86) PCT No.: PCT/IB2021/060323

§ 371 (c)(1),
(2) Date: May 2, 2023

(87) PCT Pub. No.: WO2022/118114

PCT Pub. Date: Jun. 9, 2022

(65) Prior Publication Data

US 2024/0010674 A1 Jan. 11, 2024

Related U.S. Application Data

(60) Provisional application No. 63/121,269, filed on Dec. 4, 2020.

(51) Int. Cl.
*C07K 1/32* (2006.01)
*B01D 37/00* (2006.01)
(Continued)

(52) U.S. Cl.
CPC ................ *C07K 1/32* (2013.01); *B01D 37/00* (2013.01); *B01D 39/1623* (2013.01);
(Continued)

(58) Field of Classification Search
CPC .... B01D 2239/0618; B01D 2239/0622; B01D 2239/1216; B01D 2239/1233;
(Continued)

(56) References Cited

U.S. PATENT DOCUMENTS 3,876,738 A 4/1975 Marinaccio et al.
3,928,517 A 12/1975 Knight et al.
(Continued)

FOREIGN PATENT DOCUMENTS

WO 1997012901 A1 4/1997
WO 2013009491 A2 1/2013
(Continued)

OTHER PUBLICATIONS

Amersham Biosciences, "8-1165-29AA Selecting Hollow Fiber Cartridges and Systems", 2003, 116 pages.
(Continued)

*Primary Examiner* — Jennifer Wecker
(74) *Attorney, Agent, or Firm* — HYLTON-RODIC LAW PLLC

(57) ABSTRACT

Described herein is a method of purifying a target molecule from an aqueous biological composition, the method comprising: (a) contacting a cationic polymer and the aqueous biological composition to form a mixture, the mixture comprising a bio-polymer complex and the target non-binding molecule in a liquid, wherein the bio-polymer complex has an average particle diameter of at least 50 micrometers; (b) providing a filtering unit comprising (i) a housing having an inlet and an outlet, (ii) a porous, continuous filter medium which is fluidly connected to the inlet and the outlet, and (iii)
(Continued)

a collection region upstream from the porous, continuous filter medium; (c) adding the mixture to the inlet; and (d) allowing the mixture to separate in the filtering unit, whereby the bio-polymer complex collects in the collection region and the target non-binding molecule passes through the filter medium, and wherein the majority of flow of the liquid through the porous, continuous filter medium is not substantially parallel with the direction of gravity.

18 Claims, 1 Drawing Sheet

(51) Int. Cl.
*B01D 39/16* (2006.01)
*B01D 71/56* (2006.01)
*C07K 1/34* (2006.01)
*C07K 1/36* (2006.01)
*C07K 16/06* (2006.01)

(52) U.S. Cl.
CPC ................ *B01D 71/56* (2013.01); *C07K 1/34* (2013.01); *C07K 1/36* (2013.01); *C07K 16/065* (2013.01); *B01D 2239/0618* (2013.01); *B01D 2239/0622* (2013.01); *B01D 2239/1216* (2013.01); *B01D 2239/1233* (2013.01); *B01D 2239/1266* (2013.01)

(58) Field of Classification Search
CPC ............ B01D 2239/1266; B01D 37/00; B01D 39/1623; B01D 71/56; C07K 1/32; C07K 1/34; C07K 1/36; C07K 16/065
See application file for complete search history.

(56) References Cited

U.S. PATENT DOCUMENTS 4,118,531 A 10/1978 Hauser
4,529,256 A 7/1985 Kretzschmar et al.
4,707,265 A 11/1987 Barnes, Jr. et al.
4,726,989 A 2/1988 Mrozinski
4,867,881 A 9/1989 Kinzer
5,120,594 A 6/1992 Mrozinski
5,260,360 A 11/1993 Mrozinski et al.
5,458,782 A 10/1995 Hou et al.
5,962,544 A 10/1999 Waller, Jr.
6,056,529 A 5/2000 Meyering et al.
6,267,916 B1 7/2001 Meyering et al.
6,413,070 B1 7/2002 Meyering et al.
6,464,084 B2 10/2002 Pulek
6,712,966 B1 * 3/2004 Pulek .................... B01D 39/18
210/489
6,776,940 B2 8/2004 Meyering et al.
6,779,411 B1 8/2004 Spurgeon
6,939,466 B2 9/2005 Pulek et al.
7,178,676 B2 2/2007 Pulek et al.
7,338,692 B2 3/2008 Smith et al.
8,945,896 B2 2/2015 Rasmussen et al.
9,296,847 B2 3/2016 Rasmussen et al.
10,005,814 B2 6/2018 Rasmussen et al.
10,087,405 B2 10/2018 Swanson et al.
10,722,848 B2 * 7/2020 Hester .................... B01D 71/78
2008/0023385 A1 * 1/2008 Baker, Jr. ................ C02F 1/004
210/195.1
2011/0259812 A1 10/2011 Marks et al.
2018/0265542 A1 9/2018 Rasmussen et al.

FOREIGN PATENT DOCUMENTS

WO 2016153915 A1 9/2016
WO 2017217930 A1 12/2017
WO 2021105864 A1 6/2021

OTHER PUBLICATIONS

Davies, C.N., “The Separation of Airborne Dust and Particles” in the Institution of Mechanical Engineers, London, Proceedings, 1B, 1952, pp. 185-213.
International Search Report received for PCT International Application No. PCT/IB2021/060323, mailed on Feb. 23, 2022, 5 pages.
Tarleton, et al. “Solid Liquid Separation: Equipment Selection and Process Design”, 2007, Elsevier Science, pp. 64-66, 75, 142 and 143.
Wente, “Manufacture of Superfine Organic Fibers” Naval Research Laboratories Report No. 4364 (111437), May 1954, 19 pages.
Wente, “Superfine Thermoplastic Fibers”, Industrial and Engineering Chemistry, Aug. 1956, vol. 48, No. 8, pp. 1342-1346.

* cited by examiner

FILTRATION UNIT AND A METHOD FOR BIOMATERIAL PURIFICATION

TECHNICAL FIELD

A filtration unit and a method of separating a desired biological molecule (such as an antibody, protein, enzyme, etc.) from an aqueous biological composition (such as a harvest from a cell culture or fermentation process) is disclosed.

BACKGROUND

Manufacturing of large scale or commercial quantities of therapeutically useful targeted biomaterials, such as proteins, can be accomplished by growing cells that are engineered to produce a desired protein in bioreactors under controlled conditions. The technology used involves, for example, the fermentation of microorganisms which have been altered through recombinant DNA techniques or the culturing of mammalian cells which have been altered through hybridoma techniques. The cells are suspended in a broth which contains the salts, sugars, proteins, and various factors necessary to support the growth of particular cells. The desired product may be either secreted by the cells into the broth or retained within the cell body. The harvested broth is then processed to recover, purify, and concentrate the desired product.

SUMMARY

Typically, post-harvest processing of cell cultures and/or fermentation products involves a primary recovery step, which removes larger particle solids, cells and cell debris (typically by continuous centrifugation or depth filter) and a secondary recovery step, which removes smaller sub-micron particles (typically a two-stage filtration train comprised of a depth filter followed by a membrane filter). After this recovery, the filtrate, comprising the targeted molecule is then exposed to extensive downstream processing, including column chromatography (such as protein A or cation-exchange) to yield high quantities of the purified target molecule.

Advances in manufacture of biomaterials have produced cell cultures having, for example higher antibody titers, which increases cell culture density and lengthens culture duration. This translates into higher levels of process-related impurities such as host cell proteins and DNA, lipids, colloids and cell debris. These higher impurity levels present challenges to the recovery, purification, and/or concentration of the target molecule. For example, the higher PCV (packed cell volume) concentrations can exceed the capacity of stack disk centrifugation and if the sub-micron cellular debris is not sufficiently removed, it can result in the fouling of downstream processes such as the depth filters and/or membrane filters.

Thus, there is need in the art for improved methods related to the recovery, isolation, and/or purification of targeted biomaterials such as proteins, enzymes and antibodies, involving procedures that are less time consuming, allow more efficient recovery of the desired product, and/or can be operated at lower pressure drops.

In one aspect, a method of purifying a non-binding target molecule from an aqueous biological composition comprising a binding species is disclosed, the method comprising:

(a) contacting a cationic polymer and the aqueous biological composition to form a mixture, the mixture comprising a bio-polymer complex and the target non-binding molecule in a liquid, wherein the bio-polymer complex has an average particle diameter of at least 50 micrometers;

(b) providing a filtering unit comprising (i) a housing having an inlet and an outlet, (ii) a porous, continuous filter medium which is fluidly connected to the inlet and the outlet, and (iii) a collection region upstream from the porous, continuous filter medium;

(c) adding the mixture to the inlet; and (d) allowing the mixture to separate in the filtering unit, wherein a majority of flow of the liquid through the porous, continuous substrate is not substantially parallel to the direction of gravity and the bio-polymer complex collects in the collection region and the target non-binding molecule passes through the outlet.

In another aspect, a kit is disclosed, wherein the kit comprises a cationic polymer and a filtering unit comprising a porous, continuous filter medium.

In another aspect, a filtration unit is disclosed. The filtration unit comprising a housing having an inlet, an outlet and a porous, continuous filter medium fluidly connecting the inlet and the outlet, wherein the filtration unit comprises a collection region positioned between the inlet and the porous, continuous filter medium wherein the collection region is at least 40 L per 1 $m^2$ of frontal surface area of the porous, continuous filter media.

The above summary is not intended to describe each embodiment. The details of one or more embodiments of the invention are also set forth in the description below. Other features, objects, and advantages will be apparent from the description and from the claims.

Figure 1:
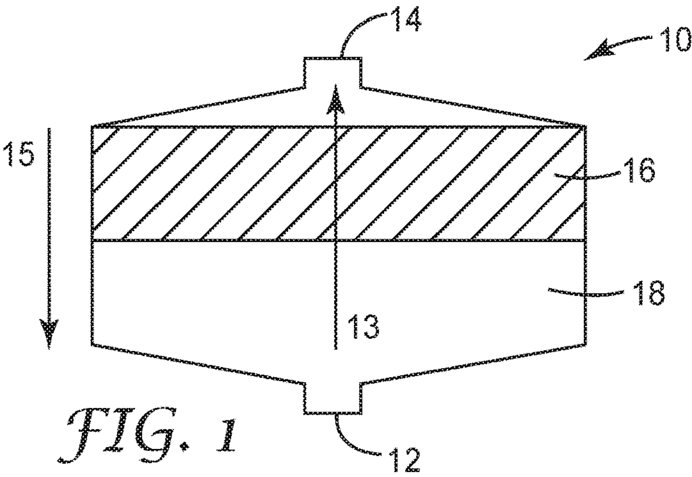
FIG. 1 is a cross-sectional view of an exemplary filtering unit.

It should be understood that numerous other modifications and embodiments can be devised by those skilled in the art, which fall within the scope and spirit of the principles of the disclosure. The figures are not drawn to scale.

DETAILED DESCRIPTION

As used herein, the term

"Alkyl" means a linear or branched, cyclic or acyclic, saturated monovalent hydrocarbon having from one to about twelve carbon atoms (C1-C12), e.g., methyl, ethyl, 1-propyl, 2-propyl, pentyl, and the like.

"Alkylene" means a linear saturated divalent hydrocarbon having from one to about twelve carbon atoms (i.e., C1-C12) or a branched saturated divalent hydrocarbon having from three to about twelve carbon atoms (i.e., C3-C12), e.g., methylene, ethylene, propylene, 2-methylpropylene, pentylene, hexylene, and the like.

"Alkenyl" means a linear unsaturated monovalent hydrocarbon having from two to about twelve carbon atoms (i.e., C2-C12) or a branched unsaturated hydrocarbon having from three to about twelve carbon atoms (i.e., C3-C12).

"Aryl" means a monovalent aromatic, such as phenyl, naphthyl and the like.

"Guanidinyl" means a functional group selected from at least one of guanidine and biguanide.

(Hetero)alkyl includes alkyl and heteroalkyl groups, the later comprising one or more in-chain heteroatoms such as oxygen or nitrogen atoms. They can be linear or branched, cyclic or acyclic, saturated monovalent moeities having from one to about twelve carbon atoms.

(Hetero)alkylene includes divalent alkylene and heteroalkylene groups, the later comprising one or more in-chain heteroatoms such as oxygen or nitrogen atoms.

(Hetero)aryl includes aryl and heteroaryl groups, the later comprising one or more in-chain heteroatoms such as oxygen or nitrogen atoms.

(Hetero)arylene includes divalent aromatic arylene and heteroarylene groups, the later comprising one or more in-chain heteroatoms such as oxygen or nitrogen atoms.

"a", "an", and "the" are used interchangeably and mean one or more.

"and/or" is used to indicate one or both stated cases may occur, for example A and/or B includes, (A and B) and (A or B).

As used herein, recitation of ranges by endpoints includes all numbers subsumed within that range (e.g., 1 to 10 includes 1.4, 1.9, 2.33, 5.75, 9.98, etc.).

As used herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

The term "aqueous biological composition" refers to any aqueous composition comprising a desired macromolecule along with undesired macromolecules all of biological origin. The composition need not be exclusively of biological origin. In one embodiment, the aqueous biological composition is the harvest fluid of a fermentation or cell culture process.

The desired macromolecule of biological origin is the target molecule that is to be isolated and/or purified. Such target molecules include, for example, proteins such as enzymes, antibodies, or other desired proteins. Typically, the target molecule, also called the non-binding target molecule, is cationic in nature at the pH of the requisite fluid, such as the aqueous biological composition or an aqueous buffer solution. In one embodiment, the method of the present disclosure may be used in the separation of cationic proteins, more preferably monoclonal antibodies from the undesired components of a harvest fluid.

The aqueous biological composition also comprises a variety of near neutral or negatively charged macromolecules of biological origin, such as whole cells and insoluble cell debris, and soluble impurities, including protein impurities, such as host cell proteins, DNA, and chromatin, which need to be separated from the target molecule. These species are sometimes referred to as binding species due to their propensity to bind to cationic groups.

Cell debris generally refers to components of lysed (broken) cells, including the cell wall lipids, organelles (e.g., mitochondria, lysosomes, vesicles, and the like), and proteinaceous aggregates. Typically, cell debris are larger, predominantly negatively-charged material that can clog filters. Turbidity is one way to measure the concentration of cell debris in a fluid, where the higher the turbidity value the more cell debris present. For example, in one embodiment, the aqueous biological composition has a turbidity of at least 100, 200, 500, or even 1000 NTU (nephelometric turbidity unit) and at most 6000, 5000, 4000, 3000, or even 2000 NTU. In some embodiments, the solids content in the aqueous biological composition is so large that the turbidity cannot be measured.

Cells and cell debris, typically negatively charged, include those derived from archaea, bacteria, and eukaryotes. Bacteria include, but are not limited to, Gram-negatives such as *Pseudomonas* species, *Escherichia coli, Helicobacter pylori*, and *Serratia marcesens*; Gram-positives such as *Staphylococcus* species, *Enterococcus* species, *Clostridium* species, *Bacillus* species, and *Lactobacillus* species; bacteria that do not stain traditionally by Gram's method such as *Mycobacterium* species, and non-vegetative forms of bacteria such as spores. Eucaryotes include, but are not limited to, animal cells, algae, hybridoma cells, stem cells, cancer cells, plant cells, fungal hyphae, fungal spores, yeast cells, parasites, parasitic oocysts, insect cells, and helminthes. Proteins, include, but are not limited to, natural proteins, recombinant proteins, enzymes, and host cell proteins. Viruses include, but are not limited to, enveloped species such as Herpesviruses, Poxviruses, Adenoviruses, Papovaviruses, Coronaviruses, retroviruses such as HIV, and Plasmaviridae; and non-enveloped species such as Caliciviridae, Corticoviridae, Myoviridae, and Picornaviridae.

Undesired proteins having a near neutral or negative charge, such as protein impurities and host cell proteins, are also typically present in the aqueous biological composition. In one embodiment, the aqueous biological composition has a host cell protein concentration of at least 50,000; 100,000 or even 200,000 ng/mL and at most 2,000,000; 1,000,000; or even 500,000 ng/mL (nanograms/milliliter). These soluble proteins are smaller in nature and need to be separated from the target molecule.

DNA, a nucleotide sequence, which is the blueprint for replication of the cell, may also be present in the aqueous biological composition and is also negatively charged. In one embodiment, the aqueous biological composition has a concentration of DNA of at least $10^5$, $10^6$, $10^7$, $10^8$, or even $10^9$ picograms/mL.

These above referenced biological materials, including others such as bacterial spores, nucleic acids, endotoxins, and viruses, need to be separated from the target molecule before therapeutic use.

Typically, the aqueous biological composition is a buffered solution, which resists changes to pH. In one embodiment, the aqueous biological composition has a high salt concentration. The term "salt" is meant to include all low molecular weight ionic species which contribute to the conductivity of the solution. Many process solutions used in biopharmaceutical or enzyme manufacture have conductivities in the range of 15-30 mS/cm (milliSiemens per centimeter) (approximately 150-300 mM salt) or more.

In some embodiment, the aqueous biological composition has a packed cell volume of at least 1, 2, 5, 8, 10, or even 15 wt % and as high as 20 wt %.

The liquid portion of the aqueous biological composition is primarily water. Generally, the aqueous biological composition is substantially free (i.e., less than 1, 0.5, 0.1 or even 0.05 wt % or even non-detectable) of organic solvents.

In one embodiment, the target molecule is present at a concentration of at least 0.1, 0.2, 0.5, 1, 2, 4, 6, or even 10 grams/liter (g/L) in the aqueous biological composition. In one embodiment, the desired macromolecules of biological origin are present at a concentration of at most 10, 12, 15, 18, or even 20 g/L in the aqueous biological composition. In some embodiments, the concentration of the desired macromolecules of biological origin is even higher than 20 g/L in the aqueous biological composition.

The present disclosure concerns a method of separating a targeted biological molecule from an aqueous biological composition. The primary and/or secondary recovery steps described above can be replaced by the methods disclosed herein, where a cationic polymer is used to flocculate near neutral and/or negatively charged biomaterials from an aqueous biological composition forming a bio-polymer complex. A porous, continuous filter medium is then used to separate the bio-polymer complex from the aqueous liquid comprising the targeted biological molecule.

A cationic polymer is contacted with the aqueous biological composition. The cationic polymer comprises groups having the requisite affinity for binding near neutral or negatively charged macromolecules of biological origin, such as whole cells, cellular debris, host cell proteins, DNA, etc. which bind to the cationic polymer forming a bio-polymer complex.

The cationic polymer disclosed herein is water soluble or water dispersible. As used herein, the term "water soluble" refers to a material that can be dissolved in water. The solubility is typically at least about 0.1 gram per milliliter of water. As used herein, the term "water dispersible" refers to a material that is not water soluble, but that can be emulsified or suspended in water. The cationic polymer also comprises a functional group attached (e.g., indirectly or directly covalently bonded) to the polymer backbone, wherein the functional group is a guanidinyl group, which is sufficiently basic that it is substantially protonated in aqueous media having a pH of 5.0-8.0. For example, suitable such basic groups include groups with a $pK_a$ in water of their protonated cationic form of at least 9, preferably at least 10, and more preferably at least 12.5, or, meaning that the group is capable of being protonated by the water.

In one embodiment, the cationic polymer comprises at least one guanidinyl-containing side chain according to Formula (I):

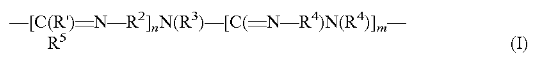

(I)

In Formula (I), the group $R^1$ is hydrogen, C1-C12 (hetero) alkyl, or C5-C12 (hetero)aryl, or a residue of the polymer chain. The group $R^2$ is a covalent bond, a C2-C12 (hetero) alkylene, or a C5-C12 (hetero)arylene. The group $R^3$ is hydrogen, C1-C12 (hetero)alkyl, or C5-C12 (hetero)aryl, or can be a residue of the polymer chain when n is 0. Each group $R^4$ is independently hydrogen, C1-C12 (hetero)alkyl, or C5-C12 (hetero)aryl. The group R is hydrogen, C1-C12 (hetero)alkyl, C5-C12 (hetero)aryl, or $—N(R^4)_2$. The variable n is equal to 0 or 1 depending on the precursor polymer used to form the guanidinyl-containing polymer. The variable m is equal to 1 or 2 depending on whether the cationic group is a guanidinyl or biguanidinyl group.

Most cationic polymers have more than one pendent guanidinyl-containing group. The number of pendent guanidinyl-containing groups can be varied depending the method used to prepare the cationic polymer. In some embodiments, the cationic polymer comprises at least 1, 2, 4, or even 5 pendent guanidinyl-containing groups. In some embodiments, the cationic polymer comprises at most 10, 20, 40, 60, 80, 100, 200, 500, or even 1000 pendent guanidinyl-containing groups.

The cationic guanidinyl-containing polymers may be derived from amino-containing polymers and/or carbonyl-containing polymers.

In some embodiments, the cationic polymer is prepared by reaction of an amino-containing polymer precursor with a guanylating agent. Such guanidinyl-containing polymers and how to make them may be found, for example, in U.S. Pat. No. 10,087,405 (Swanson et al.), herein incorporated by reference. When an amino-containing polymer is used, typically n in Formula (I) is 0.

Examples of amino-containing polymers suitable for use include, but are not limited to, polyvinylamine, poly(N-methylvinylamine), polyallylamine, polyallylmethylamine, polydiallylamine, poly(4-aminomethylstyrene), poly(4-aminostyrene), poly(acrylamide-co-methylaminopropylacrylamide), poly(acrylamide-co-aminoethylmethacrylate), polyethylenimine, polypropylenimine, polylysine, polyaminoamides, and polydimethylamine-epichlorohydrin-ethylenediamine.

Other useful amino-containing polymers that have primary or secondary amino end groups include, but are not limited to, dendrimers (hyperbranched polymers) formed from polyamidoamine (PAMAM) and polypropylenimine. Exemplary dendrimeric materials formed from PAMAM are commercially available under the trade designation STARBURST (PAMAM) dendrimer (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, WI). Dendrimeric materials formed from polypropylenimine are commercially available under the trade designation DAB-Am from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, PA), polyethylenimine polymers that are available under the trade designation LUPASOL (e.g., LUPASOL FG, PR 8515, Waterfree, P, and PS) from BASF Corporation (Rensselaer, NY), polyethylenimine polymers such as those available under the trade designation CORCAT P-600 from EIT Company (Lake Wylie, SC), and polyamide resins such as those available from Cognis Corporation (Cincinnati, OH) under the traded designation VERSAMID series of resins that are formed by reacting a dimerized unsaturated fatty acid with alkylene polyamines.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand.

The additional ligands can be readily incorporated into the amino-containing polymers by alkylation or acylation procedures well known in the art. For example, amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

In some embodiments, the cationic polymer is prepared by reaction of a carbonyl-containing polymer and a suitable guanylating agent for reaction with a carbonyl group. Such carbonyl-containing polymers and how to make them maybe found, for example, in U.S. Pat. No. 10,087,405 (Swanson et al.), herein incorporated by reference.

When a carbonyl-containing polymer is used, typically n in Formula (I) is 1 and the polymer comprises a group of —C(O)—$R^1$, which can be reacted with a guanylating agent. The carbonyl group —C(O)—$R^1$ is an aldehyde group (when $R^1$ is hydrogen) or a ketone group (when $R^1$ is a (hetero)alkyl or (hetero)aryl). Although the carbonyl-group can be part of the polymeric backbone or part of a pendant group from the polymeric backbone, it is typically a pendant group.

In some embodiments, the carbonyl-containing polymer is the polymerized product of a monomer composition that includes an ethylenically unsaturated monomer having a carbonyl group, preferably a ketone group. Suitable monomers having a carbonyl group include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

In other embodiments, the carbonyl-containing polymer is the polymerized product of a monomer composition that includes carbon monoxide and one or more ethylenically unsaturated monomer (i.e., the carbonyl-containing polymer is a carbon monoxide copolymer). An example of a carbon monoxide containing copolymer is ELVALOY 741, a terpolymer of ethylene/vinyl acetate/carbon monoxide from DuPont (Wilmington, DE, USA).

In addition to carbon monoxide and/or an ethylenically unsaturated monomer with a carbonyl group (e.g., a ketone group), the monomer composition used to form that carbonyl-containing polymer can optionally further comprise ethylenically unsaturated hydrophilic monomer units. As used herein, "hydrophilic monomers" are those polymerizable monomers having water miscibility (water in monomer) of at least 1 weight percent preferably at least 5 weight percent without reaching a cloud point, and contain no functional groups that would interfere with the binding of biological substances to the ligand group. The carbonyl-containing polymer may include, for example, 0 to 90 weight percent of the hydrophilic monomers in the monomer composition. If present, the hydrophilic monomer can be present in an amount in a range of 1 to 90 weight percent, 1 to 75 weight percent, 1 to 50 weight percent, 1 to 25 weight percent, or 1 to 10 weight percent based on based a total weight of the monomer composition.

The hydrophilic groups of the hydrophilic monomers may be neutral and/or have a positive charge. Hydrophilic monomers with an ionic group can be neutral or charged depending on the pH conditions. Hydrophilic monomers are typically used to impart a desired hydrophilicity (i.e. water solubility, miscibility, or dispersibility, or to enable the polymer to be wet by or absorb water) to the carbonyl-containing polymer.

Some exemplary hydrophilic monomers that are capable of providing a positive charge are amino (meth)acrylates or amino (meth)acrylamides of Formula (II) or quaternary ammonium salts thereof. The counter ions of the quaternary ammonium salts are often halides, sulfates, phosphates, nitrates, and the like.

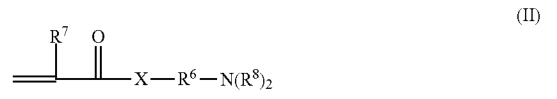

(II)

In Formula (II), the group X is oxy (i.e., —O—) or —$NR^3$— where $R^3$ is hydrogen, $C_1$-$C_{12}$ (hetero)alkyl, or $C_5$-$C_{12}$ (hetero)aryl. The group $R^6$ is a $C_2$ to $C_{10}$ alkylene, preferably a C2-C6 alkylene. The group $R^7$ is independently hydrogen or methyl. Each $R^8$ is independently hydrogen, alkyl, hydroxyalkyl (i.e., an alkyl substituted with a hydroxy), or aminoalkyl (i.e., an alkyl substituted with an amino). Alternatively, the two $R^8$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

It will be understood with respect to Formula (II) that the depicted ethylenically unsaturated (meth)acryloyl group ($CH_2$=C($R^7$)—C(O)— group) may be replaced by another ethylenically unsaturated group of reduced reactivity, such as vinyl, vinyloxy, allyl, allyloxy, and acetylenyl.

In some embodiments of Formula (II), both $R^8$ groups are hydrogen. In other embodiments, one $R^8$ group is hydrogen and the other is an alkyl having 1 to 10, 1 to 6, or 1 to 4 carbon atoms. In still other embodiments, at least one of $R^8$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the $R^8$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to, imidazolyl. The heterocyclic group can be fused to an additional ring such as a benzene, cyclohexene, or cyclohexane. Exemplary heterocyclic groups fused to an additional ring include, but are not limited to, benzimidazolyl.

Exemplary amino acrylates (i.e., "X" in Formula (II) is oxy) include N,N-dialkylaminoalkyl (meth)acrylates such as, for example, N,N-dimethylaminoethyl(meth)acrylate, N,N-dimethylaminoethylacrylate, N,N-diethylaminoethylacrylate, N,N-dimethylaminopropyl(meth)acrylate, N-tert-butylaminopropyl(meth)acrylate, and the like.

Exemplary amino (meth)acrylamides (i.e., "X" in Formula (II) is —$NR^3$—) include, for example, N-(3-aminopropyl)methacrylamide, N-(3-aminopropyl)acrylamide, N-[3-(dimethylamino)propyl]methacrylamide, N-[3-(dimethylamino)propyl]acrylamide, N-(3-imidazolylpropyl) methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzimidazolylpropyl) acrylamide, and N-(3-benzimidazolylpropyl) methacrylamide.

Exemplary quaternary salts of the monomers of Formula (II) include, but are not limited to, (meth)acrylamidoalkyltrimethylammonium salts (e.g., 3-methacrylamidopropyltrimethylammonium chloride and 3-acrylamidopropyltrimethylammonium chloride) and (meth) acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups to the polymer include the dialkylaminoalkylamine adducts of alkenylazlactones (e.g., 2-(diethylamino)ethylamine, (2-aminoethyl)trimethylammonium chloride, and 3-(dimethylamino)propylamine adducts of vinyldimethylazlactone) and diallylamine monomers (e.g., diallylammonium chloride and diallyldimethylammonium chloride).

In some preferred embodiments, the optional hydrophilic monomer may have an ethylenically unsaturated group such as a (meth)acryloyl group and a poly(alkylene oxide) group.

For example, the hydrophilic monomer can be a poly (alkylene oxide) mono(meth)acrylate compounds, where the terminus is a hydroxy group, or an alkyl ether group. Such monomers are of the general Formula (III).

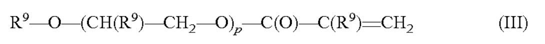

$$R^9—O—(CH(R^9)—CH_2—O)_p—C(O)—C(R^9)═CH_2 \quad (III)$$

In Formula (III), each $R^9$ is independently hydrogen or a $C_1$-$C_4$ alkyl. The variable p is at least 2 such as, for example, 2 to 100, 2 to 50, 2 to 20, or 2 to 10.

In one embodiment, the carbonyl containing polymer comprises a poly(alkylene oxide) group (depicted as —(CH($R^9$)—CH2-O)$_p$—), wherein the poly(alkylene oxide) group is a poly(ethylene oxide). In another embodiment, the poly (alkylene oxide) group is a poly(ethylene oxide-co-propylene oxide). Such copolymers may be block copolymers, random copolymers, or gradient copolymers.

Other representative examples of suitable hydrophilic monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylacrylamide; N-octyl acrylamide; poly(alkoxyalkyl) (meth)acrylates including 2-(2-ethoxyethoxy)ethyl (meth)acrylate, 2-ethoxyethyl (meth) acrylate, 2-methoxyethoxyethyl (meth)acrylate, 2-methoxyethyl methacrylate, polyethylene glycol mono (meth)acrylates; alkyl vinyl ethers, including vinyl methyl ether; and mixtures thereof. Preferred hydrophilic monomers include those selected from the group consisting of dimethylacrylamide, 2-hydroxyethyl (meth)acrylate, and N-vinylpyrrolidinone.

In some embodiments, the monomer composition used to form the carbonyl-containing polymer can optionally include a hydrophobic monomer. As used herein, the term "hydrophobic monomer" refers monomers having a water miscibility (water in monomer) that is less than 1 weight percent. The hydrophobic monomers can be used in amounts that do not deleteriously affect the binding performance of the guanidinyl-containing monomer polymer and/or the water dispersibility of the guanidinyl-containing polymer. When present, the hydrophobic monomer is typically present in an amount in a range of 1 to 20 weight percent, 1 to 10 weight percent, or 1 to 5 weight percent based on a total weight of monomers in the monomer composition.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_1$-$C_{30}$ alkyl groups. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and dialkylacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

Additional useful classes of hydrophobic monomers further include vinyl monomers such as vinyl acetate, styrenes, and alkyl vinyl ethers, and maleic anhydride.

The guanidinyl-containing polymers comprising the side chain according to Formula (I) are often the reaction product of a carbonyl-containing polymer precursor and a guanylating agent of Formula (IV).

(IV)

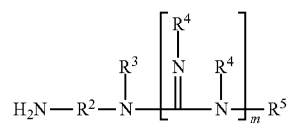

In Formula (IV), the group $R^2$ is a covalent bond, C2-C12 (hetero)alkylene, or C5-C12 (hetero)arylene. Group $R^3$ is hydrogen, C1-C12 (hetero)alkyl, or C5-C12 (hetero)aryl. Each $R^4$ is independently hydrogen, C1-C12 (hetero)alkyl, or C5-C12 (hetero)aryl. Group $R^5$ is H, C1-C12 (hetero) alkyl, or C5-C12 (hetero)aryl, or —$N(R^4)_2$. The variable m is equal to 1 or 2.

For ease of description, the carbonyl-containing polymer can be represented by the formula Polymer-C(═O)—$R^1$. The carbonyl group can be in the backbone or in a pendant group but is usually in a pendant group. When reacted with a guanylating agent of Formula (IV), the carbonyl group in the carbonyl-containing polymer undergoes a condensation reaction with a terminal amine group of the guanylating agent. The guanidinyl-containing polymer typically has guanidinyl-containing pendant groups of Formula (V).

(V)

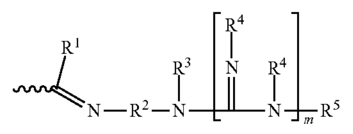

The groups $R^2$, $R^3$, $R^4$, and $R^5$ are the same as described above for Formula (IV) and the wavy line represents the polymer. The group of formula

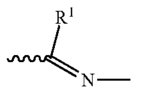

in Formula (V) is the linkage formed between the terminal amine of the ligand compound of Formula (IV) and the carbonyl group of the carbonyl-containing polymer. The wavy line denotes the attachment site of the group via a covalent bond to the rest of the polymer. Group $R^1$ is hydrogen (when the carbonyl group is an aldehyde group), C1-C12 (hetero)alkyl (when the carbonyl group is a ketone group and the ketone group is part of a pendant group), or C5-C12 (hetero)aryl (when the carbonyl group is a ketone group and the ketone group is part of a pendant group), or a residue of the polymer chain (when the carbonyl group is a group in the backbone of the carbonyl-containing polymer). In most embodiments, the group of Formula (V) is part of a pendant group of the guanidinyl-containing polymer.

In other embodiments, the guanidyl-containing polymer may be prepared in which the imine linking group (~~C($R^1$)═N—) is reduced to an amine linking group (~~CH($R^1$)—NH—). This may be affected by treating the extant ligand functional polymer with a reducing agent, such as sodium cyanoborohydride, or the reduction may be affected in situ by adding the reducing agent to the reaction mixture of the carbonyl functional (co)polymer and the compound of Formula V.

In many embodiments, some but not all of the carbonyl groups of the carbonyl-containing polymer are reacted with the guanylating agent of Formula (IV). Typically, at least 0.1 mole percent, at least 0.5 mole percent, at least 1 mole percent, at least 2 mole percent, at least 10 mole percent, at least 20 mole percent, or at least 50 mole percent of the carbonyl groups in the carbonyl-containing polymer precursor are reacted with the guanylating agent. Up to 100 mole percent, up to 90 mole percent, up to 80 mole percent, or up to 60 mole percent of the carbonyl groups can be reacted with the guanylating agent. For example, the guanylating agent can be used in amounts sufficient to functionalize 0.1 to 100 mole percent, 0.5 to 100 mole percent, 1 to 90 mole percent, 1 to 80 mole percent, 1 to 60 mole percent, 2 to 50 mole percent, 2 to 25 mole percent, or 2 to 10 mole percent of the carbonyl groups in the carbonyl-containing polymer.

Rather than reacting a precursor polymer with a guanylating agent to prepare a guanidinyl-containing polymer, the guanidinyl-containing polymer can be prepared by free radical polymerization of a guanidinyl-containing monomer, which refers to a monomer having an ethylenically unsaturated group and a guanidinyl-containing group. Example guanidinyl-containing monomers are of Formula (VI) and (VII).

(VI)

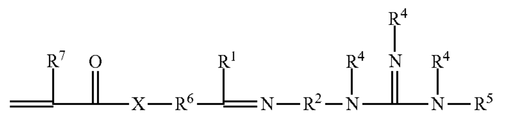

-continued (VII)

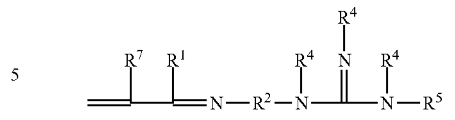

In Formulas (VI) and (VII), group $R^1$ is hydrogen, C1-C12 alkyl, or C5-C12 (hetero)aryl. Group $R^2$ is a covalent bond, a C2 to C12 alkylene, a C5-C12 (hetero)arylene, a divalent group of formula

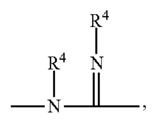

or a divalent group of formula

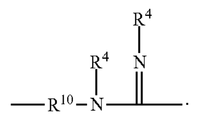

Group $R^{10}$ is C2 to C12 alkylene, or C5-C12 (hetero) arylene. Each $R^3$ is independently hydrogen, hydroxyl, C1-C12 alkyl, or C5-C12 (hetero)aryl. $R^3$ is preferably hydrogen or C1-C4 alkyl. Group $R^4$ is hydrogen, C1-C12 alkyl, C5-C12 (hetero)aryl, or —N($R^3$)$_2$, wherein $R^3$ is independently hydrogen, hydroxyl, C1-C12 alkyl, or C5-C12 (hetero)aryl. Preferably, $R^4$ is hydrogen or C1-C4 alkyl. Group X is oxy or —N$R^3$—, wherein $R^3$ is hydrogen, hydroxyl, C1-C12 alkyl, or C5-C12 (hetero)aryl. Group $R^6$ is a C2 to C12 alkylene. Group $R^7$ is hydrogen or $CH_3$.

The amount of cationic polymer that is added relative to the amount of aqueous biological composition can vary over a wide range. In one embodiment, the amount of cationic polymer added to the aqueous biological composition is at least 0.01, 0.02, 0.05, 0.1, 0.5, 1, 5, 10, 20, 50, 100, 250, or even 500 micrograms/mL. In one embodiment, the amount of cationic polymer added to the aqueous biological composition is at most 50, 100, 250, 500, 1000, 2000, 5000, 7500, or even 10000 micrograms/mL. The optimal amount of cationic polymer added will depend upon the concentration of the near neutral or negatively charged biomaterials present (i.e., binding species) in the aqueous biological composition. Typically, the amount of cationic polymer relative to the amount of binding species will be in the range of 0.01% to 100% by weight, preferably 0.05%-30% by weight, more preferably about 0.1%-10% by weight.

The cationic polymer is contacted with the aqueous biological composition for a time sufficient for the near neutral and negatively charged binding species to interact with the cationic polymer to form a bio-polymer complex. The cationic polymer binds (for example ionically, hydrogen bonding, etc.) with the near neutral or negatively charged macromolecules. In one embodiment, the aqueous biological composition and the cationic polymer are agitated while they are in intimate contact with each other to form the bio-polymer complex. Suitable mixing methods include shaking by hand, laboratory agitators, mechanical and/or magnetic stirrers, and passing through a static mixer, for example. Agitation may be performed for any length of time sufficient to effectively bind biological compounds to the cationic polymer and may depend on the volume of material agitated. In some embodiments, the agitation is preferably less than 60 seconds, less than 45 seconds, or even less than 30 seconds. In other embodiments, the agitation may be as long as 20 minutes or more, for example.

The resulting mixture comprises the bio-polymer complex and the target molecule in an aqueous solution/suspension. In one embodiment, the target molecule may be disposed (dissolved or suspended) in the solution when the solution comprises from at least 50, 60, 70, 80, 90 or even 100 mM salt; and at most 125, 150, 200, 250, 300, 350, or even 400 mM salt.

In many embodiments, the cationic polymer, being positively charged in aqueous media, will bind near neutral or negatively charged species to the cationic functional group while other species (e.g., positively charged proteins such as monoclonal antibodies) will be excluded or repelled from the cationic polymer. In addition, the cationic polymer may be derived from one or more ionic monomers. In particular, the cationic polymer may comprise additional ionic groups that are positively charged at the selected pH of the aqueous biological solution to enhance electrostatic charge repulsion of proteins, such as monoclonal antibodies, many of which are charged positive at neutral pH.

The bio-polymer complex has an average particle diameter of at least 45, 50, 60, 70, 75 or even 80 micrometers. In one embodiment, the bio-polymer complex has an average particle diameter of at most 100, 110, 120, 130, 140, 150, 160, 170, 180, 190, 200, 220, 240, 260, 280, 300, 350, 400, 450, 500, or even 1000 micrometers. The average particle diameter may be determined using techniques known in the art such as reflectance or light scattering. Typically, the resulting bio-polymer complex is not soluble in water and precipitates out of an aqueous solution.

In another embodiment, the bio-polymer complex is suspended in an aqueous solution using techniques known in the art, such as mechanical agitation. Following suspension, the aqueous mixture then is subsequently (for example, immediately) filtered as described below to separate the target molecule from the bio-polymer complex. Advantageously, in the present disclosure, the bio-polymer complex does not need to settle out of the mixture prior to filtering.

The mixture is passed through a filtering unit. As shown in FIG. 1, filtering unit 10 comprises a housing having inlet 12 and outlet 14 defining a liquid flow path therebetween. A porous, continuous filter medium 16 is positioned in the liquid flow path between the inlet and outlet, such that the liquid entering the filtering unit passes through the porous, continuous filter medium before exiting the unit. Arrow 13 indicates the net direction of the majority of fluid flow through porous, continuous filter medium 16 from inlet 12 to outlet 14. Collection region 18 is positioned upstream from the porous, continuous filter medium. As depicted in FIG. 1, the majority of the bulk fluid flow through the porous, continuous filter medium (depicted by arrow 13) is counter, in exactly the opposite direction, to the direction of gravity, depicted by arrow 15.

The mixture comprising the bio-polymer complex and the target biological molecule in a liquid is added to the inlet and allowed to interact with the porous, continuous filter medium. The clarified liquid (or filtrate), containing the target macromolecule, exits via the outlet. The filtering unit is positioned such that the direction of the majority of flow of the liquid through the porous, continuous filter medium is not substantially parallel with the direction of Earth's gravity. As used herein, a majority of the flow means greater than 50, 60, 75, 85, or even 95% by volume of the flow of the liquid through the filter medium.

Although not wanting to be limited by theory, it is believed that when filtering the mixture parallel and in the same direction as gravity, the bio-polymer complex can deposit on the top (or head) of the porous, continuous filter medium forming a "cake" and/or could intercalate into the porous, continuous filter medium. This could result in clogging of the porous, continuous filter medium; could reduce fluid flow through the filter medium; and/or increase back pressure of the filtering unit. If substantial enough, the clogging could prevent the exit of the target non-binding molecule from the outlet. The present application has discovered that operating the filtering unit such that the majority of flow of the liquid is not substantially parallel to and in the same direction of gravity, can lead to efficient separation of the target non-binding molecule from the bio-polymer complex and collection of the target non-bonding molecule. As used herein, gravity refers to Earth's gravity.

Figure 2:
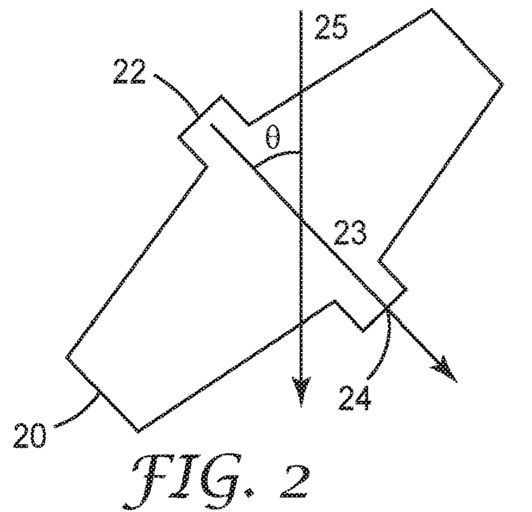
FIG. 2 is a cross-sectional view of an exemplary filtering unit.

The direction of the flow of the bulk liquid through the porous, continuous filter medium of the present disclosure is not substantially parallel to the direction of gravity. Not substantially parallel, as used herein, means that the direction of the majority of the fluid flow through the porous, continuous filter medium is greater than 30, 40, or even 60 degrees from the direction of gravity. In one embodiment, the direction of the majority of the fluid flow through the porous, continuous filter medium is at most 330, 320, 300, 270, or even 180 degrees from the direction of gravity. As shown in FIG. 2, filtering unit 20, with inlet 22 and outlet 24, has a fluid flow in the direction of arrow 23. A majority of the fluid flow through the porous, continuous filter medium of filtering unit 20 is at 0 degrees from the direction of gravity, shown by arrow 25. The angle θ can be measured as the degrees that the majority of the fluid flow through the filter medium (shown by arrow 23) differs from the direction of gravity, shown by arrow 25. In one embodiment, the bulk fluid flow through the porous, continuous filter medium is perpendicular to the direction of gravity (e.g., θ is about 90 degrees or about 270 degrees). In another embodiment, the bulk fluid flow through the porous, continuous filter medium is exactly opposite to the direction of gravity (e.g., 0 is about 180 degrees). In one embodiment, the direction of the bulk fluid flow through the porous, continuous filter medium is counter to the direction of gravity, where the direction of the bulk fluid flow through the porous, continuous filter medium flows in the direction of the Earth to the sky (i.e., θ is about 90 to about 270 degrees).

The filtering unit comprises a collection region, which is upstream from the porous, continuous filter medium. Often times in filtration, the void volume (in other words, the volume of liquid phase contained within the filtration unit) is kept to a minimum to reduce the dilution of the filtrate. In the present disclosure, the collection region, specifically, the volume between the inlet and the frontal surface of the porous, continuous filter medium of the filtration unit, is sufficiently large. This region, referred to herein as the collection region, is where the bio-polymer complex collects so as not to clog the porous, continuous filter medium. In one embodiment, the collection region is at least 40, 45, 50, 75, 100, 150, or even 200 L per frontal surface area of the porous, continuous filter medium (in $m^2$). The surface area of the porous, continuous filter medium can be determined using the geometric surface area. For example, in the case of a circular frontal area, the frontal surface area can be determined using the equation $\pi^2$, where r is the radius. Generally, the collection region is large enough to allow for the collection of the bio-polymer complex, but, not so large that the filtration unit becomes unwieldy to handle (for example, 2000 L per 1 $m^2$ of frontal surface area of the porous, continuous filter medium).

The filtering unit disclosed herein comprises a porous, continuous filter medium. The filter medium is continuous, meaning that it is a single article across the width of the filtering unit and not a collection of articles across the width of the filtering unit, such as loose fibers. Exemplary continuous, porous filter media include a nonwoven substrate or a microporous web. The filter media are porous, meaning the articles comprise minute holes (or pores) throughout, enabling the flow of fluid from the inlet to the outlet. In one embodiment, the pores have an average diameter of at least 0.1, 0.2, 0.5, 0.8, 1, 2, 5, 10, 20, or even 40 micrometers; and at most 50, 75, 100, 125, 150, 175, or even 200 micrometers. In one embodiment, the porous, continuous filter medium of the present disclosure has an average pore diameter which is symmetric in the direction of the bulk liquid flow. In other words, the porous, continuous filter medium does not comprise a larger average pore size at one end (e.g., the inlet end) of the porous, continuous filter medium.

The nonwoven substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by carded, air laid, wet laid, spunlaced, spunbonding, electrospinning or melt-blowing techniques, such as melt-spun or melt-blown, or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g., air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the non-woven webs may be made from a single type of fiber or two or more fibers that differ in the type of thermoplastic polymer and/or thickness.

Staple fibers may also be present in the web. The presence of staple fibers generally provides a loftier, less dense web than a web of only melt blown microfibers. Preferably, no more than about 20 weight percent staple fibers are present, more preferably no more than about 10 weight percent. Such webs containing staple fiber are disclosed in U.S. Pat. No. 4,118,531 (Hauser).

The nonwoven article may optionally further comprise one or more layers of scrim. For example, either or both major surfaces may each optionally further comprise a scrim layer. The scrim, which is typically a woven or nonwoven reinforcement made from fibers, is included to provide strength to the nonwoven article. Suitable scrim materials include, but are not limited to, nylon, polyester, fiberglass, polyethylene, polypropylene, and the like. The average thickness of the scrim can vary. Typically, the average thickness of the scrim ranges from about 25 to about 100 micrometers, preferably about 25 to about 50 micrometers. The layer of the scrim may optionally be bonded to the nonwoven article. A variety of adhesive materials can be used to bond the scrim to the polymeric material. Alternatively, the scrim may be heat-bonded to the nonwoven.

The microfibers of the nonwoven substrate typically have an effective fiber diameter of from at least 0.5, 1, 2, or even 4 micrometers and at most 20, 18, 16, 15, 10, 8, or even 6 micrometers, as calculated according to the method set forth in Davies, C. N., "The Separation of Airborne Dust and Particles," Institution of Mechanical Engineers, London, Proceedings 1B, 1952. The nonwoven substrate preferably has a basis weight in the range of at least 5, 10, 20, or even 50 g/$m^2$; and at most 800, 600, 400, 200, or even 100 g/$m^2$. The minimum tensile strength of the nonwoven web is about 4.0 Newtons. It is generally recognized that the tensile strength of nonwovens is lower in the machine direction than in the cross-web direction due to better fiber bonding and entanglement in the latter.

Further details on the manufacturing method of nonwoven webs may be found in Wente, Superfine Thermoplastic Fibers, 48 INDUS. ENG. CHEM. 1342 (1956), or in Wente et al., Manufacture of Superfine Organic Fibers (Naval Research Laboratories Report No. 4364, 1954).

Nonwoven web loft is measured by solidity, a parameter that defines the solids fraction in a volume of web. Lower solidity values are indicative of greater web loft. Useful nonwoven substrates have a solidity of less than 20% or even less than 15%. Solidity is a unitless fraction typically represented by α:

$$\alpha = m_f \div \rho_f \times L_{nonwoven}$$

where $m_f$ is the fiber mass per sample surface area, which $\rho_f$ is the fiber density; and $L_{nonwoven}$ is the nonwoven thickness. Solidity is used herein to refer to the nonwoven substrate itself and not to the functionalized nonwoven. When a nonwoven substrate contains mixtures of two or more kinds of fibers, the individual solidities are determined for each kind of fiber using the same $L_{nonwoven}$ and these individual solidities are added together to obtain the web's solidity, α.

The nonwoven substrate may be formed from fibers or filaments made of any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipoyliminohexamethylene), poly(iminoadipoyliminodecamethylene), and polycaprolactam. Suitable polyimides include poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols) including, poly(ethylene-co-vinyl alcohol).

The microporous membrane is a porous polymeric substrate (such as sheet or film) comprising micropores with a mean flow pore size, as characterized by ASTM Standard Test Method No. F316-03, "Standard Test Methods for Pore Size Characteristics of Membrane Filters by Bubble Point and Mean Flow Pore Test," of less than 5 micrometers. In one embodiment, the microporous membrane has a mean flow pore size of at least 0.1, 0.2, 0.5, 0.8, or even 1 micrometer; and at most 5, 3, or even 2 micrometers. The desired pore size may vary depending on the application. The microporous membrane can have a symmetric or asymmetric (e.g., gradient) distribution of pore size in the direction of fluid flow.

In one embodiment, the average pore size for a non-woven may be determined by the equation $d_f((2\alpha/\pi)^{(-1/2)}-1)$, where $d_f$ is the effective fiber diameter and $\alpha$ is web solidity. The effective fiber diameter is typically 3 to 20 micrometers for the fibers of a non-woven. The effective fiber diameter can be calculated according to the method set forth in Davies, C. N., "The Separation of Airborne Dust and Particles" in the Institution of Mechanical Engineers, London, Proceedings, 1B, 1952. In one embodiment, the non-woven membrane has a mean flow pore size of at least 12 micrometer; and at most 64 micrometers.

The microporous membrane may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(iminoadipolyliminohexamethylene), poly(iminoadipolyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

In one embodiment, the microporous membrane is a solvent-induced phase separation (SIPS) membrane. SIPS membranes are often made by preparing a homogeneous solution of a polymer in first solvent(s), casting the solution into desired shape, e.g. flat sheet or hollow fiber, contacting the cast solution with another second solvent that is a non-solvent for the polymer, but a solvent for the first solvent (i.e., the first solvent is miscible with the second solvent, but the polymer is not). Phase separation is induced by diffusion of the second solvent into the cast polymer solution and diffusion of the first solvent out of the polymer solution and into the second solvent, thus precipitating the polymer. The polymer-lean phase is removed and the polymer is dried to yield the porous structure. SIPS is also called Phase Inversion, or Diffusion-induced Phase Separation, or Nonsolvent-induced Phase Separation, such techniques are commonly known in the art. Microporous SIPS membranes are further disclosed in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. No. 3,928,517 (Knight et al.), U.S. Pat. No. 4,707,265 (Knight et al.), and U.S. Pat. No. 5,458,782 (Hou et al.).

In another embodiment, the microporous membrane is a thermally-induced phase separation (TIPS) membrane. TIPS membranes are often prepared by forming a homogenous solution of a thermoplastic material and a second material (such as a diluent), and optionally including a nucleating agent, by mixing at elevated temperatures in plastic compounding equipment, e.g., an extruder. The solution can be shaped by passing through an orifice plate or extrusion die, and upon cooling, the thermoplastic material crystallizes and phase separates from the second material. The crystallized thermoplastic material is often stretched. The second material is optionally removed either before or after stretching, leaving a porous polymeric structure. Microporous TIPS membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. TIPS membranes comprising PVDF are further described in U.S. Pat. No. 7,338,692 (Smith et al.).

The nonwoven substrate and the microporous membranes may be treated to provide a cationic surface charge, for example, grafted with cation-containing monomers or cationically-ionizable monomers. "Cationically-ionizable" includes monomers that can be made cationic in solutions of appropriate pH. Such monomers include: amino (meth)acrylates or amino (meth)acrylamides, quaternary ammonium salts, and/or guanidyl-containing groups as described above. Such techniques and monomers are known in the art. See for example, U.S. Pat. No. 10,722,848 (Hester, et al.), herein incorporated by reference.

Separation of the target molecule from the bio-polymer complex is accomplished by collection of the biopolymer complex within the collection region, while the target molecule and any other non-complex molecules in a liquid can pass through the porous, continuous filter medium. The liquid having passed through the porous, continuous filter medium, herein referred to as the filtrate, is collected. The filtrate, comprising the target molecule can then be further treated to isolate and/or concentrate the target molecule.

The porous, continuous filter medium can be a column or planar filter medium that is housed within a filtering unit such as the one shown in FIG. 1. Typically, the planar disc or plug of filtration media (i.e., porous, continuous filter medium), can vary in size depending on the amount of mixture to filter. For example, for small batches (i.e., less than 1 liter) of mixture, a cartridge-style syringe filter unit may be used. As the volume of the mixture increase, the diameter of the disc can increase, from for example, 1 inch diameter discs to 8 inch diameter discs for filtering 1 liter mixtures or more.

Figure 3:
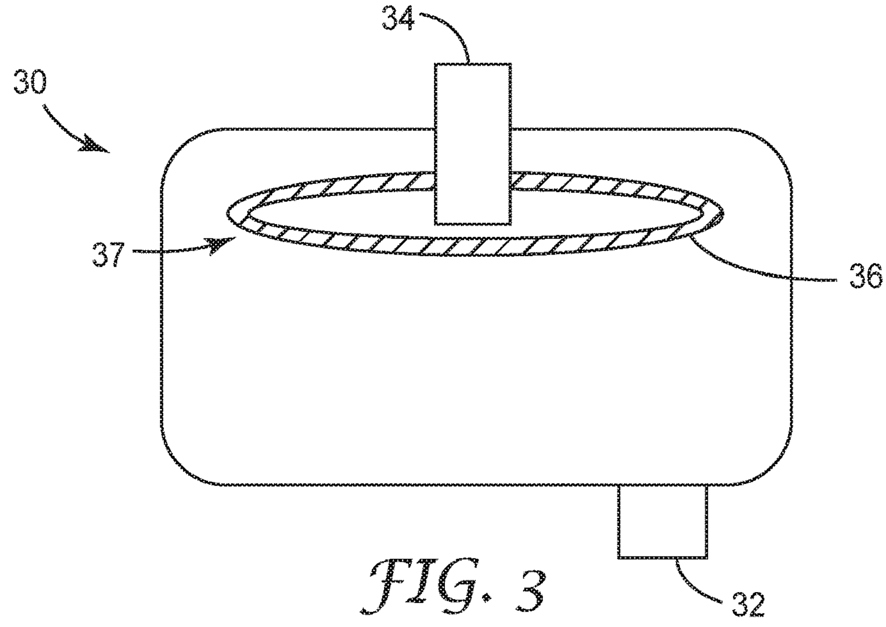
FIG. 3 is a cross-sectional view of an exemplary filtering unit.

As the volume of mixture increase (for example, greater than 5 liters), it may be helpful to use a filtering unit comprising a lenticular filter or plurality of lenticular filters. FIG. 3 depicts a cross-sectional view of an encapsulated lenticular filter design. Filter unit 30 comprises lenticular filter 37 encased in a housing. Lenticular filter 37 comprises porous, continuous filter medium 36. The mixture is added into filter unit 30 via inlet 32. The liquid flows from around the lenticular filter, passing through porous, continuous filter medium 36 and the filtrate travels from the interior of the lenticular filter out through outlet 34. Although FIG. 3 is described in an operation wherein the fluid flow is from the outside of the lenticular cell into the interior, the lenticular cell may also be run in the reverse direction, wherein the fluid flow is from the inside of the lenticular cell and proceeds outward. Examples of lenticular filter cells and methods of making lenticular filter cells may be found, for example, in U.S. Pat. No. 6,464,084 (Pulek); U.S. Pat. No. 6,939,466 (Pulek); U.S. Pat. No. 7,178,676 (Pulek et al.); and U.S. Pat. No. 6,712,966 (Pulek et al); and in U.S. Pat. Publ. No. 2011/0259812 (Marks et al).

The aqueous biological solution often comprises buffers, electrolytes, and/or sugars needed for cell growth or fermentation, but these components can impact the performance of the traditional filters used in recovery and isolation of the target molecule and thus, the process solution (e.g., the aqueous biological solution) is diluted to decrease the ionic concentration. In one embodiment of the present disclosure, there is no dilution of the aqueous biological solution prior to contact with the cationic polymer and/or contact with the continuous filter medium.

It has been discovered in the present application that the combination of particle size of the bio-polymer complex with the configuration of the porous, continuous filter medium, allows for the high capacity separation of cell debris and other near neutral or negatively charged components in the aqueous biological composition from the target biological molecule, a high capacity for substantial reduction of DNA from the fluid, and/or a high degree of host cell protein reduction, while also minimizing the number of process steps.

In one embodiment, the method of the present disclosure enables clarification of the aqueous biological composition, yielding a filtrate having a turbidity of less than 20, 15, 10, 5, or even 4 NTU.

Exemplary embodiments of the present disclosure are as follows:

Embodiment 1. A method of purifying a target non-binding molecule from an aqueous biological composition containing a binding species, the method comprising:

(a) contacting a cationic polymer and the aqueous biological composition to form a mixture, the mixture comprising a bio-polymer complex and the target non-binding molecule in a liquid, wherein the bio-polymer complex has an average particle diameter of at least 50 micrometers;

(b) providing a filtering unit comprising (i) a housing having an inlet and an outlet, (ii) a porous, continuous filter medium which is fluidly connected to the inlet and the outlet, and (iii) a collection region upstream from the porous, continuous filter medium;

(c) adding the mixture to the inlet; and (d) allowing the mixture to separate in the filtering unit, whereby the bio-polymer complex collects in the collection region and the target non-binding molecule passes through the filter medium, and wherein a majority of flow of the liquid through the filter medium is not substantially parallel to the direction of gravity.

Embodiment 2. The method of embodiment 1, wherein the average diameter of the pores in the porous, continuous filter medium is symmetric in the direction of liquid flow.

Embodiment 3. The method of any one of the previous embodiments, wherein the porous, continuous filter medium has a pore size of at least 0.1 micrometers and at most 200 micrometers.

Embodiment 4. The method of any one of the previous embodiments, wherein the porous, continuous filter medium has a pore size of at least 0.8 micrometers and at most 50 micrometers.

Embodiment 5. The method of any one of the previous embodiments, wherein the porous, continuous filter medium is a nonwoven substrate.

Embodiment 6. The method of any one of embodiments 1-4, wherein the porous, continuous filter medium is a porous membrane.

Embodiment 7. The method of any one of the previous embodiments, wherein the porous, continuous medium has a frontal surface area and wherein the collection region has a volume of at least 40 L per 1 $m^2$ of frontal surface area.

Embodiment 8. The method of any one of the previous embodiments, wherein the flow of the liquid through the porous, continuous filter medium is in a direction counter to gravity.

Embodiment 9. The method of any one of the previous embodiments, wherein the flow of the liquid through the porous, continuous filter medium is in a direction from 30 to 90 degrees from the direction of gravity.

Embodiment 10. The method of any one of the previous embodiments, wherein the net direction of the fluid flow is not parallel to the direction of gravity.

Embodiment 11. The method of any one of the previous embodiments, wherein the cationic polymer is a water soluble or water dispersible polymer.

Embodiment 12. The method of any one of the previous embodiments, wherein the cationic polymer is functionalized with guanidinyl groups.

Embodiment 13. The method of embodiment 12, wherein the cationic polymer comprises groups of the formula:

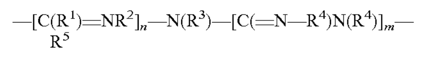

$$—[C(R^1)═NR^2]_n—N(R^3)—[C(═N—R^4)N(R^4)]_m— \quad R^5$$

wherein $R^1$ is a H, C1-C12 alkyl, C5-C12 (hetero)aryl, or a residue of the polymer chain;

$R^2$ is a covalent bond, a C2-C12 (hetero)alkylene, or a C5-C12 (hetero)arylene; each $R^3$ is independently H, C1-C12 alkyl, or C5-C12 (hetero)aryl;

each $R^4$ is H, C1-C12 alkyl or alkylene, C5-C12 (hetero) aryl or (hetero)arylene, cyano, or —C(═NH)—N ($R^2$)—Polymer;

n is 0 or 1; and m is 1 or 2.

Embodiment 14. The method of any one of the previous embodiments, wherein the cationic polymer is further functionalized with quaternary ammonium groups.

Embodiment 15. The method of any one of the previous embodiments, wherein the cationic polymer is derived from an amino polymer.

Embodiment 16. The method of embodiment 15, wherein the amino polymer is selected from the group consisting of polyethylenimine, polylysine, polyaminoamides, polyallylamine, polyvinylamine, polydimethylamine-epichlorohydrin-ethylenediamine, and dendrimers formed from polyamidoamine (PAMAM) and polypropylenimine.

Embodiment 17. The method of any one of embodiments 14-16, wherein 0.1 to 100 mole percent of the available amino groups of the amino polymer are functionalized with guanidinyl groups.

Embodiment 18. The method of embodiment 17, wherein the guanidinyl groups are in the amino polymer chain.

Embodiment 19. The method of any one of the previous embodiments, wherein the cationic polymer is derived from a carbonyl polymer.

Embodiment 20. The method of embodiment 19, wherein the carbonyl polymer is selected from the group consisting of; acrolein, vinyl methyl ketone, vinyl ethyl ketone, vinyl isobutyl ketone, diacetone (meth)acrylamide, acetonyl acrylate, carbon monoxide copolymer, and diacetone (meth) acrylate (co)polymers.

Embodiment 21. The method of any one of the previous embodiments, wherein 0.01 to 10,000 micrograms of cationic polymer is added per mL of the aqueous biological composition.

Embodiment 22. The method of any one of the previous embodiments, wherein the aqueous biological composition comprises cellular material.

Embodiment 23. The method of any one of the previous embodiments, wherein the biological composition is derived from a cell culture or fermentation process.

Embodiment 24. The method of any one of the previous embodiments, wherein the bio-polymer complex has an average particle diameter of at most 200 micrometers.

Embodiment 25. The method of any one of the previous embodiments, wherein the liquid comprises water.

Embodiment 26. The method of any one of the previous embodiments, further comprising suspending the bio-polymer complex in the liquid prior to addition to the filtering unit.

Embodiment 27. The method of any one of the previous embodiments, wherein immediately following step (a), the mixture is added to the inlet.

Embodiment 28. The method of any one of the previous embodiments, wherein at least a portion of the porous, continuous filter medium comprises at least one of polyolefins, fluorinated polymers, chlorinated polymers, polyesters, polyamides, vinyl acetate homopolymers and copolymers, and hydrolyzed derivatives vinyl acetate homopolymers and copolymers, polyether sulfones, and polyimides.

Embodiment 29. The method of any one of the previous embodiments, wherein at least a portion of the porous, continuous filter medium is hydrophilic.

Embodiment 30. The method of any one of the previous embodiments, wherein at least a portion of the porous, continuous filter medium is hydrophilically modified.

Embodiment 31. The method of any one of the previous embodiments, wherein the porous, continuous filter medium is grafted.

Embodiment 32. The method of embodiment 31, wherein the porous, continuous filter medium has a modified surface layer comprising a grafted acrylic polymer comprising 10 to 100 percent by weight of a cationic or cationically-ionizable monomer unit.

Embodiment 33. The method of embodiment 32, wherein the grafted acrylic polymer further comprises a divalent residue of a polyether (meth)acrylate.

Embodiment 34. The method of any one of embodiments 32-33, wherein the grafted acrylic polymer further comprises 0.1 to 90 percent by weight of at least one non-ionizable hydrophilic monomer unit.

Embodiment 35. The method of any one of the previous embodiments, wherein the target non-binding molecule comprises at least one of a protein, an enzyme, or an antibody.

Embodiment 36. A kit comprising:

(a) a filtering unit comprising a porous, continuous filter medium; and (b) a cationic polymer.

Embodiment 37. A filtration unit comprising a housing having an inlet, an outlet, and a porous, continuous filter medium fluidly connecting the inlet and the outlet, wherein the porous, continuous filter medium has a frontal surface area and wherein the filtration vessel comprises a collection region positioned between the inlet and the porous, continuous filter medium, wherein the collection region has a volume of at least 40 L per 1 $m^2$ of the frontal surface area.

Embodiment 38. A filter unit of embodiment 37, wherein the filtration unit is a housing comprising at least one lenticular device, the lenticular device comprising a separator element;

an edge seal;

wherein the separator element comprises a central core in fluid communication with the fluid inlet;

a first side; and a second side; and wherein the filtration unit further comprises a media disk comprising a porous, continuous filter medium positioned on the first side of the separator element and having an outer circumferential edge and an inner circumferential edge; wherein the outer circumferential edges of the media disk are connected by the edge seal and the inner circumferential edge of the media disk is connected to the central core.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Missouri, or may be synthesized by conventional methods.

The following abbreviations are used in this section: cm=centimeter, g=grams, kGy=kiloGray, kV=kilovolt, L=liter, mL=milliliter, mm=millimeter, mM=millimolar, N=normal, NMR=nuclear magnetic resonance, ° C.=degrees Celsius, mol=moles, ppm=parts per million, and IR=infrared.

Materials

Diacetone acrylamide, and VAZO 67 free-radical initiator were obtained from the Sigma-Aldrich Corporation, St. Louis, MO.

Aminoguanidine hydrochloride was obtained from TCI America, Portland, OR.

N-vinylpyrrolidone (NVP) was obtained from Ashland Specialty Chemicals, Covington, KY.

Glycidyl methacrylate (GMA) was obtained from the Dow Chemical Company, Midland, MI.

Preparatory Example 1 [PE1; Guanylated Polyethylenimine (G-PEI)]

Polyethylenimine (PEI), MW (molecular weight)=60,000 g/mol (100 grams of a 50 weight % solution in water; obtained from ACROS Organics, Geel, Belgium), was charged to a 1 L flask and deionized water (259 g) was added to the flask to reduce the percent solids content to about 25%. O-methylisourea hemisulfate (36.9 g) was added to the flask and the resulting solution was mechanically stirred at ambient temperature for about 20 hours. Analysis by NMR spectroscopy indicated conversion to the desired product having 25% of the amine groups of PEI (primarily the primary amine groups) converted to guanidines. Concentrated hydrochloric acid (38 g) was used to titrate the mixture to about pH 7 (measured using pH paper). Percent solids was determined to be 21.0% using a Mettler Toledo moisture balance analyzer (model number HR73, obtained from the Mettler Toledo Corporation, Columbus, OH).

Preparatory Example 2 [PE2; Poly(diacetoneacrylamide guanylhydrazone (pDAAGH)]

Diacetone acrylamide (160 g), ethanol (240 g) and VAZO 67 free-radical initiator (0.8 g) were charged to a 1000 mL creased round bottomed 3-necked flask having a thermowell port. The reaction flask was equipped with an overhead stirrer, nitrogen inlet and cold water condenser. The mixture was purged with a slow stream of nitrogen gas for 5 minutes and then heated at 60° C. (using a heating mantle) with stirring for 20 hours to convert the monomer to polymer. Ethanol (133 g) was added to dilute the polymer solution to about 30% by weight. A portion of this polymer solution (253.3 g) was placed in a round bottomed flask equipped with an overhead stirrer. Aminoguanidine hydrochloride (49.7 g) was dissolved in deionized water (150 g) and then added to the reaction flask. Concentrated hydrochloric acid (0.5 mL) was added and the solution was stirred for 20 hours at ambient temperature. IR spectroscopy and $^1$H-NMR analysis confirmed the formation of poly(diacetoneacrylamide guanylhydrazone). The reaction mixture was sequentially submitted to vacuum in order to remove most of the ethanol; neutralized to pH 7 by the addition of 1 N NaOH; and finally adjusted to about 20% solids by the addition of deionized water.

Preparatory Example 3 [PE-3; Poly(diallyldimethylammonium chloride) (pDADMAC)]

Poly(diallyldimethylammonium chloride) (pDADMAC) (average MW 400,000-500,000 g/mol; 20 weight % in water) solution was obtained from Sigma-Aldrich and diluted to 10 weight % in deionized water.

Preparatory Example 4. Nonwoven Filter Medium

A melt-blown polypropylene microfiber nonwoven sheet was prepared using TOTAL 3860X polypropylene resin (obtained from Total Petrochemicals USA, Deer Park, TX). The nonwoven sheet had an effective fiber diameter of 4.2 micrometers, a basis weight of 200 grams per square meter, solidity of 10%, average pore size of 12 micrometers, and a substrate thickness of 0.9 mm.

Preparatory Example 5. Nonwoven Filter Medium

A melt-blown polypropylene microfiber nonwoven sheet was prepared using TOTAL 3860X polypropylene resin. The nonwoven sheet had an effective fiber diameter of 8 micrometers, a basis weight of 200 grams per square meter, solidity of 10%, average pore size of 24 micrometers, and a substrate thickness of 1.6 mm.

Preparatory Example 6. Nonwoven Filter Medium

A melt-blown polypropylene microfiber nonwoven sheet was prepared using TOTAL 3860X polypropylene resin. The nonwoven sheet had an effective fiber diameter of 16 micrometers, a basis weight of 200 grams per square meter, solidity of 10%, average pore size of 47 micrometers, and a substrate thickness of 1.8 mm.

Preparatory Example 7. Copolymer Grafted Nonwoven Filter Medium

A sample of the nonwoven substrate of Preparatory Example 4 (21.6 cm by 21.6 cm) was purged of air under a nitrogen atmosphere in a glove box. Once the oxygen levels reached <20 ppm, the nonwoven substrate was inserted into a plastic bag and sealed.

A monomer grafting solution (150 grams) containing by weight 12% NVP, 4% GMA, 84% deionized water was added to a glass jar. The jar was capped and shaken by hand to mix the contents. The jar was then opened and the solution was sparged with nitrogen for 2 minutes to remove any dissolved oxygen from the solution. The jar was re-capped and transferred into the oxygen depleted glovebox. The jar lid was then removed to flush any residual air from the jar headspace.

The sealed bag containing nonwoven sample was removed from the glove box and irradiated to a dose level of 40 kGy by passing through a CB-300 electron beam apparatus (Energy Sciences, Inc., Wilmington, MA) in a single pass operation at a speed of approximately 5.5 meters per minute and an accelerating voltage of 300 kV. The bag containing the irradiated nonwoven sample was then returned to the glove box.

The monomer grafting solution was added to the plastic bag containing the nonwoven sample. The bag was sealed and the solution was distributed through the nonwoven sample using a hand roller so that the nonwoven sheet was uniformly covered with the solution. The bag was sealed and the nonwoven sample was maintained flat in the bag for 3 hours. The resulting copolymer grafted nonwoven sample was removed from the bag and boiled in deionized water for one hour. The sample was removed from the water bath and air dried at room temperature for 24 hours. Discs (25 mm in diameter) were punched from the dried sample.

Preparatory Example 8. Copolymer Grafted Nonwoven Filter Medium

The same grafting procedure as described in Preparatory Example 7 was followed with the exception that the copolymer grafted nonwoven filter medium was prepared from the nonwoven filter medium of Preparatory Example 5.

CHO Cell Culture Preparation

A monoclonal antibody-producing Chinese hamster ovary (CHO) cell culture was produced using a fed-batch process over 10-12 days in a READYTOPROCESS WAVE 25 bioreactor (GE Healthcare, Chicago, IL). The culture was harvested at 80% viability into 2 L sterile media bottles. The harvested cell culture was refrigerated overnight at 4° C. to settle cells and cell debris. Concentrated biomass was achieved by pumping supernatant out of the container.

Packed cell volume (PCV) of the concentrated biomass was determined by centrifugation of 200 microliters of CHO cell culture with a fixed angle rotor down at 2,500 rcf (relative centrifugal force) for 1 minute in a PCV cell counting tube (obtained from Sigma-Aldrich). PCV was adjusted to the desired level using supernatant fluid. The CHO culture was stored at 4° C. for up to 3 days.

Particle Size Measurement of Bio-polymer Complex

Fifty milliliters of CHO cell culture prepared as described above (8% PCV) was added to a glass beaker and stirred at 100 rpm using a magnetic stir bar. A single polymer selected from Preparatory Examples 1-3 was diluted in water to 10 weight %. The diluted polymer sample was added using a micro channel pipet to the stirring CHO cell culture over a period of 90 seconds to achieve a final concentration of 0.1 weight %. The mixture was stirred for 15 minutes while the particle size of the resulting bio-polymer complex was measured. A focused Beam Reflectance Measurement probe (ParticleTrack G400; Mettler Toledo, Columbus, OH) was inserted 2 inches into the liquid so that it was not positioned in the vortex. Particle size was tracked and evaluated using iC FBRM 4.4 software (Mettler Toledo). The mean particle sizes (micrometers) measured at the 15 minute time point are reported in Table 1.

TABLE 1

| Polymer | Mean Particle Size of the Bio-Polymer Complex (micrometers) |
|---|---|
| PE1 (G-PEI) | 127 |
| PE2 (pDAAGH) | 81 |
| PE3 (pDADMAC) | 40 |

Example 1

Fifty milliliters of CHO cell culture (8% PCV) was added to a glass beaker and stirred at 100 rpm using a magnetic stir-bar. G-PEI polymer of Preparatory Example 1 was diluted in water to 10 weight %. The diluted polymer sample was added using a micro channel pipet to the stirring CHO cell culture over a period of 90 seconds to achieve a final concentration of 0.1 weight %. After 15 minutes of continued stirring, the resulting bio-polymer complex suspension was immediately submitted to a filtering unit (described below) for further processing.

A 25 mm disc of nonwoven filter medium prepared according to Preparatory Example 4 was inserted in the filtering unit. The disc was held in place using o-rings resulting in an exposed disc frontal surface area of 284 $mm^2$. The filtering unit contained a straight, cylindrical polycarbonate body with a cap attached to one end of the filtering unit body. The cap contained an inlet port and a vent port. The opposite end contained an outlet port with a stopcock. The collection region was 81 L per 1 $m^2$ of frontal surface area A pressure sensor was placed upstream of the inlet port. Using a PendoTech (Princeton, NJ) normal flow filtration system with MASTERFLEX L/S PharMed BPTflex size 16 tubing (Cole-Parmer Company, Vernon Hills, IL) connected to the inlet port, the bio-polymer complex suspension was pumped at 2 mL/minute into the filtering unit. The filtering unit was operated in the inverted position (i.e. the filtering unit was aligned in a vertical orientation with the outlet port above the inlet port so that the pumped liquid flowed through the substrate in the opposite direction of the direction of gravity). The filtrate was collected through the outlet port into a receiving vessel. The collection of filtrate was stopped when either (a) the inlet pressure reached 5 psi (pounds per square inch or 34 kiloPascal) or (b) when no visible liquid was observed in the unit and no liquid was observed exiting the outlet port over a two minute period. A single trial was conducted and the results for yield (%) and turbidity (NTU) of the recovered filtrate are reported in Table 2.

The turbidity of the collected filtrate was measured using a Hach 2100AN Turbidimeter (Hach Company, Loveland, CO). Yield was determined by following equation:

$$\text{Yield }(\%)=[(\text{volume of filtrate recovered})/(\text{volume of cell culture liquid})]\times 100.$$

The volume of cell culture liquid was determined by multiplying the initial volume of cell culture by the PCV value.

Example 2

The same procedure as described in Example 1 was followed with the exception that the nonwoven filter medium of Preparatory Example 5 was used, instead of the nonwoven substrate of Preparatory Example 4. A single trial was conducted and the results for yield (%) and turbidity (NTU) of the recovered filtrate are reported in Table 2.

Example 3

The same procedure as described in Example 1 was followed with the exception that the nonwoven filter medium of Preparatory Example 6 was used, instead of the nonwoven substrate of Preparatory Example 4. A single trial was conducted and the results for yield (%) and turbidity (NTU) of the recovered filtrate are reported in Table 2.

Example 4

The same procedure as described in Example 1 was followed with the exception that the copolymer grafted nonwoven filter medium of Preparatory Example 7 was used, instead of the nonwoven filter medium of Preparatory Example 4. A single trial was conducted and the results for yield (%) and turbidity (NTU) of the recovered filtrate are reported in Table 2.

Example 5

The same procedure as described in Example 1 was followed with the exception that the copolymer grafted nonwoven filter medium of Preparatory Example 8 was used, instead of the nonwoven filter medium of Preparatory Example 4. A single trial was conducted and the results for yield (%) and turbidity (NTU) of the recovered filtrate are reported in Table 2.

Example 6

The same procedure as described in Example 1 was followed with the exception that a nylon membrane (nylon 6,6, single reinforced layer three zone membrane, nominal pore size 0.8 micron, #080ZN from 3M Purification, Inc., Meriden, CT) was used, instead of the nonwoven filter medium of Preparatory Example 4. A single trial was conducted and the results for yield (%) and turbidity (NTU) of the recovered filtrate are reported in Table 2.

Example 7

The same procedure as described in Example 1 was followed with the exception that pDAAGH polymer of Preparatory Example 2 was used to prepare the bio-polymer complex suspension, instead of G-PEI polymer of Preparatory Example 1. A single trial was conducted and the results for yield (%) and turbidity (NTU) of the recovered filtrate are reported in Table 2.

Comparative Example A

The same procedure as described in Example 1 was followed with the exception that pDADMAC polymer of Preparatory Example 3 was used to prepare the bio-polymer complex suspension, instead of G-PEI polymer of Preparatory Example 1. A single trial was conducted and the results for yield (%) and turbidity (NTU) of the recovered filtrate are reported in Table 2.

TABLE 2

Yield and turbidity results wherein the flow of liquid was in the opposite direction of gravity

| Example | Cationic Polymer | Filtering media | Yield (%) | Turbidity of Filtrate (NTU) |
|---|---|---|---|---|
| Example 1 | PE1 (G-PEI) | Preparatory Example 4 | 93 | 17 |
| Example 2 | PE1 (G-PEI) | Preparatory Example 5 | 66 | 25 |
| Example 3 | PE1 (G-PEI) | Preparatory Example 6 | 76 | 20 |
| Example 4 | PE1 (G-PEI) | Preparatory Example 7 | 68 | 16 |
| Example 5 | PE1 (G-PEI) | Preparatory Example 8 | 76 | 22 |
| Example 6 | PE1 (G-PEI) | Nylon membrane | 87 | 2 |
| Example 7 | PE2 (pDAAGH) | Preparatory Example 4 | 81 | 6 |
| Comparative Example A | PE3 (pDADMAC) | Preparatory Example 4 | 69 | 384 |

Examples 8

The same procedure as described in Example 1 was followed with the exception that the liquid was pumped at 2 mL/minute into the filtering unit with the filtering unit operated in the horizontal position (i.e. the filtering unit was placed in a horizontal orientation so that the pumped liquid flowed through the substrate in a direction perpendicular to the direction of gravity). A single trial was conducted and the results for yield (%) and turbidity (NTU) of the recovered filtrate are reported in Table 3.

Example 9

The same procedure as described in Example 8 was followed with the exception that pDAAGH polymer of Preparatory Example 2 was used to prepare the bio-polymer complex suspension, instead of G-PEI polymer of Preparatory Example 1. A single trial was conducted and the results for yield (%) and turbidity (NTU) of the recovered filtrate are reported in Table 3.

Comparative Example B

The same procedure as described in Example 8 was followed with the exception that pDADMAC polymer of Preparatory Example 3 was used to prepare the bio-polymer complex suspension, instead of G-PEI polymer of Preparatory Example 1. A single trial was conducted and the results for yield (%) and turbidity (NTU) of the recovered filtrate are reported in Table 3.

TABLE 3

Yield and turbidity results wherein the flow of liquid was perpendicular to the direction of gravity

| Example | Cationic Polymer | Yield (%) | Turbidity of Filtrate (NTU) |
|---|---|---|---|
| Example 8 | PE1 (G-PEI) | 94% | 18 |
| Example 9 | PE2 (pDAAGH) | 82% | 29 |
| Comparative Example B | PE3 (pDADMAC) | 85% | 67 |

Examples 10

The same procedure as described in Example 1 was followed with the exception that the liquid was pumped through the substrate at a 45° angle (i.e. the filtering unit was aligned as in FIG. 2 with the angle $\theta=45°$). A single trial was conducted and the results for yield (%) and turbidity (NTU) of the recovered filtrate are reported in Table 4.

Example 11

The same procedure as described in Example 10 was followed with the exception that pDAAGH polymer of Preparatory Example 2 was used to prepare the bio-polymer complex suspension, instead of G-PEI polymer of Preparatory Example 1. A single trial was conducted and the results for yield (%) and turbidity (NTU) of the recovered filtrate are reported in Table 4.

Comparative Example C

The same procedure as described in Example 10 was followed with the exception that pDADMAC polymer of Preparatory Example 3 was used to prepare the bio-polymer complex suspension, instead of G-PEI polymer of Preparatory Example 1. A single trial was conducted and the results for yield (%) and turbidity (NTU) of the recovered filtrate are reported in Table 4.

TABLE 4

Yield and turbidity results wherein the flow of liquid was at about 45 degrees from the direction of gravity

| Example | Cationic Polymer | Yield (%) | Turbidity of Filtrate (NTU) |
|---|---|---|---|
| Example 10 | PE1 (G-PEI) | 94% | 18 |
| Example 11 | PE2 (pDAAGH) | 82% | 29 |
| Comparative Example C | PE3 (pDADMAC) | 105% | 2680 |

Example 12. Filtering Units with Different Collection Region Volumes

The same procedure as described in Example 1 was followed with the exception that the filtering units tested were of different sizes and had varying collection regions. Four different filtering units having collection regions of 32, 81, 116, and 162 L per 1 $m^2$ of frontal surface area were evaluated. A single trial was conducted with each filtering unit. The results for filtrate throughput (L/1 $m^2$ of frontal surface area) and turbidity (NTU) of the recovered filtrate are reported in Table 5. Filtrate Throughput was calculated as the volume of filtrate collected divided by the frontal surface area of the nonwoven disc.

TABLE 5

Yield and turbidity results wherein the flow of liquid was in the opposite direction of gravity

| Collection Region (Liters per 1 $m^2$ of frontal surface area) | Filtrate Throughput ($L/m^2$) | Turbidity of Filtrate (NTU) |
|---|---|---|
| 32 | 60 | 3 |
| 81 | 335 | 28 |
| 116 | 486 | 20 |
| 162 | 623 | 11 |

Comparative Examples D

The same procedure as described in Example 1 was followed with the exception that the filtering unit was operated in the vertical position with the inlet port oriented above the outlet port so that the pumped liquid flowed through the substrate in the same direction as the direction of gravity (in other words, θ=0). A single trial was conducted. Collection of the filtrate was stopped due to the inlet pressure reaching 5 psi. The results for yield (%) are reported in Table 6. Turbidity of the filtrate could not be measured, because an insufficient amount of filtrate was recovered for testing.

Comparative Example E

The same procedure as described in Comparative Example D was followed with the exception that pDAAGH polymer of Preparatory Example 2 was used to prepare the bio-polymer complex suspension, instead of G-PEI polymer of Preparatory Example 1. A single trial was conducted. Collection of the filtrate was stopped due to the inlet pressure reaching 5 psi. The results for yield (%) are reported in Table 6. Turbidity of the filtrate could not be measured, because an insufficient amount of filtrate was recovered for testing.

Comparative Example F

The same procedure as described in Comparative Example D was followed with the exception that pDADMAC polymer of Preparatory Example 3 was used to prepare the bio-polymer complex suspension, instead of G-PEI polymer of Preparatory Example 1. A single trial was conducted and the results for yield (%) and turbidity (NTU) of the recovered filtrate are reported in Table 6.

TABLE 6

Yield and turbidity results wherein the flow of liquid was in the same direction as gravity

| Example | Cationic Polymer | Yield (%) | Turbidity of Filtrate (NTU) |
|---|---|---|---|
| Comparative Example D | PE1 (G-PEI) | 4% | NM |
| Comparative Example E | PE2 (pDAAGH) | 3% | NM |
| Comparative Example F | PE3 (pDADMAC) | 94% | 2606 |

NM = not measured

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A method of purifying a target non-binding molecule from an aqueous biological composition containing a binding species, the method comprising:

(a) contacting a cationic polymer and the aqueous biological composition to form a mixture, the mixture comprising a bio-polymer complex and the target non-binding molecule in a liquid, wherein the bio-polymer complex has an average particle diameter of at least 50 micrometers;

(b) providing a filtering unit comprising (i) a housing having an inlet and an outlet, (ii) a porous, continuous filter medium which is fluidly connected to the inlet and the outlet, and (iii) a collection region disposed upstream from the porous, continuous filter medium; and (c) adding the mixture to the inlet; and (d) allowing the mixture to be separated in the filtering unit, whereby the bio-polymer complex collects in the collection region and the target non-binding molecule passes through the filter medium, and wherein a majority of flow of the liquid through the filter medium is at least partially parallel to the direction of gravity.

2. The method of claim 1, wherein the average diameter of the pores in the porous, continuous filter medium is symmetric in the direction of liquid flow.

3. The method of claim 1, wherein the porous, continuous filter medium has a pore size of at least 0.1 micrometers and at most 200 micrometers.

4. The method of claim 1, wherein the porous, continuous medium has a frontal surface area and wherein the collection region has a volume of at least 40 L per 1 m2 of frontal surface area.

5. The method of claim 1, wherein the flow of the liquid through the porous, continuous filter medium is in a direction counter to gravity.

6. The method of claim 1, wherein the flow of the liquid through the porous, continuous filter medium is in a direction from 30 to 90 degrees from the direction of gravity.

7. The method of claim 1, wherein the net direction of the fluid flow is not parallel to the direction of gravity.

8. The method of claim 1, wherein the cationic polymer is a water soluble or water dispersible polymer.

9. The method of claim 1, wherein the cationic polymer is functionalized with at least one of (a) guanidinyl groups, optionally according to the formula:

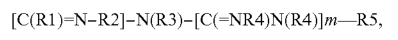

[C(R1)=N–R2]–N(R3)–[C(=NR4)N(R4)]*m*—R5, wherein

R1 is a H, C1-C12 alkyl, C5-C12 (hetero) aryl, or a residue of the polymer chain;

R2 is a covalent bond, a C2-C12 (hetero)alkylene, or a C5-C12 (hetero) arylene; each R3 is independently H, C1-C12 alkyl, or C5-C12 (hetero) aryl;

each R4 is H, C1-C12 alkyl or alkylene, C5-C12 (hetero) aryl or (hetero) arylene, cyano, or —C(═NH) N (R2)-Polymer;

n is 0 or 1; and m is 1 or 2; and (b) quaternary ammonium groups.

10. The method of claim 1, wherein the cationic polymer is derived from an amino polymer.

11. The method of claim 1, wherein the cationic polymer is derived from a carbonyl polymer.

12. The method of claim 1, wherein 0.1 to 10.000 micrograms of cationic polymer is added per mL of the aqueous biological composition.

13. The method of claim 1, wherein the bio-polymer complex has an average particle diameter of at most 200 micrometers.

14. The method of claim 1, wherein the liquid comprises water.

15. The method of claim 1, further comprising suspending the bio-polymer complex in the liquid prior to addition to the filtering unit.

16. The method of claim 1, wherein immediately following step (a), the mixture is added to the inlet.

17. The method of claim 1, wherein the porous, continuous filter medium is grafted.

18. The method of claim 17, wherein the porous, continuous filter medium has a modified surface layer comprising a grafted acrylic polymer comprising 10 to 100 percent by weight of a cationic or catatonically-ionizable monomer unit and optionally, a divalent residue of a polyether (meth) acrylate.

* * * * *